US009113778B2

(12) United States Patent
McNair

(10) Patent No.: US 9,113,778 B2
(45) Date of Patent: *Aug. 25, 2015

(54) PREDICTING NEAR-TERM DETERIORATION OF HOSPITAL PATIENTS

(71) Applicant: Cerner Innovation, Inc., Kansas City, KS (US)

(72) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/087,411

(22) Filed: Nov. 22, 2013

(65) Prior Publication Data

US 2014/0081092 A1    Mar. 20, 2014

Related U.S. Application Data

(63) Continuation of application No. 13/270,748, filed on Oct. 11, 2011, now Pat. No. 8,595,159.

(51) Int. Cl.
| | | |
|---|---|---|
| *G06F 15/18* | (2006.01) | |
| *A61B 5/00* | (2006.01) | |
| *A61B 5/021* | (2006.01) | |
| *A61B 5/024* | (2006.01) | |

(52) U.S. Cl.
CPC ............... *A61B 5/0022* (2013.01); *A61B 5/021* (2013.01); *A61B 5/024* (2013.01); *A61B 5/4884* (2013.01); *A61B 5/7246* (2013.01); *A61B 5/7264* (2013.01); *A61B 5/7275* (2013.01); *A61B 5/742* (2013.01); *A61B 5/7405* (2013.01); *A61B 5/746* (2013.01)

(58) Field of Classification Search
None
See application file for complete search history.

(56) References Cited

U.S. PATENT DOCUMENTS

2012/0108916 A1* 5/2012 Riftine ...................... 600/301

OTHER PUBLICATIONS

Álvaro Silva, Paulo Cortez, Manuel Filipe Santos, Lopes Gomes, José Neves, Mortality assessment in intensive care units via adverse events using artificial neural networks, Artificial Intelligence in Medicine, vol. 36, Issue 3, Mar. 2006, pp. 223-234.*
Pranesh Kumar and Mohamed M Shoukri. Copula based prediction models: an application to an aortic regurgitation study. BMC Medical Research Methodology 2007, 7:21. Jun. 16, 2007.*
Anthony Stell, Richard Sinnott, and Jipu Jiang. 2009. A Clinical Grid Infrastructure Supporting Adverse Hypotensive Event Prediction. In Proceedings of the 2009 9th IEEE/ACM International Symposium on Cluster Computing and the Grid (CCGRID '09). IEEE Computer Society, Washington, DC, USA, 508-513.*
Gagne, Nathalie. Developing a Non-Invasive Method to Monitor Cardiovascular Control during Orthostatic Challenge Considering the Limitation of the Finometer. University of Waterloo Masters Thesis. Waterloo, ON. Mar. 25, 2009. http://uwspace.uwaterloo.ca/handle/10012/4299.*

(Continued)

*Primary Examiner* — Jeffrey A Gaffin
*Assistant Examiner* — David H Kim
(74) *Attorney, Agent, or Firm* — Shook, Hardy & Bacon LLP

(57) ABSTRACT

Methods, systems, and computer storage media are provided for predicting a probability of acute deterioration for a specific patient. Various discrete measurements are taken regarding the patient's current health. Those measurements are used to determine a PPOD score, which is displayed for clinicians.

17 Claims, 8 Drawing Sheets

(56) References Cited

OTHER PUBLICATIONS

Fitzmaurice G., Laird N. Regression models for a bivariate discrete and continuous outcome with clustering. J Amer Stat Assoc 1995; 90:845-52.

Kojadinovic I., Yan J. Modeling multivariate distributions with continuous margins using the copula R package. J Stat Software 2010; 341-20.

Liu C., Rubin D. Ellipsoidally symmetric extensions of the general location model for mixed categorical and continuous data. Biometrika 1998; 85:673-88.

Olkin I., Tate R. Multivariate correlation models with mixed discrete and continuous variables. Ann Math Stat 1961; 32:448-65.

Regan M., Catalano P. Likelihood models for clustered binary and continuous outcomes: application to developmental toxicology. Biometrics 1999; 55:760-8.

Zeger S., Liang K. Feedback models for discrete and continuous time series. Statistica Sinica 1991; 1:51-64.

* cited by examiner

FIG. 3

| SBPCURR | \ SBPUSUAL 220 | 210 | 200 | 190 | 180 | 170 | 160 | 150 | 140 | 130 | 120 | 110 | 100 | 90 | 80 |
|---|---|---|---|---|---|---|---|---|---|---|---|---|---|---|---|
| 220 | 0.00 | 0.00 | 0.00 | 0.60 | 1.10 | 1.56 | 1.99 | 2.37 | 2.72 | 3.03 | 3.30 | 3.54 | 3.73 | 3.89 | 4.00 |
| 210 | 0.00 | 0.00 | 0.00 | 0.06 | 0.60 | 1.10 | 1.56 | 1.99 | 2.37 | 2.72 | 3.03 | 3.30 | 3.54 | 3.73 | 3.89 |
| 200 | 0.06 | 0.00 | 0.00 | 0.00 | 0.06 | 0.60 | 1.10 | 1.56 | 1.99 | 2.37 | 2.72 | 3.03 | 3.30 | 3.54 | 3.73 |
| 190 | 0.60 | 0.06 | 0.00 | 0.00 | 0.00 | 0.06 | 0.60 | 1.10 | 1.56 | 1.99 | 2.37 | 2.72 | 3.03 | 3.30 | 3.54 |
| 180 | 1.10 | 0.60 | 0.06 | 0.00 | 0.00 | 0.00 | 0.06 | 0.60 | 1.10 | 1.56 | 1.99 | 2.37 | 2.72 | 3.03 | 3.30 |
| 170 | 1.56 | 1.10 | 0.60 | 0.06 | 0.00 | 0.00 | 0.00 | 0.06 | 0.60 | 1.10 | 1.56 | 1.99 | 2.37 | 2.72 | 3.03 |
| 160 | 1.99 | 1.56 | 1.10 | 0.60 | 0.06 | 0.00 | 0.00 | 0.00 | 0.06 | 0.60 | 1.10 | 1.56 | 1.99 | 2.37 | 2.72 |
| 150 | 2.37 | 1.99 | 1.56 | 1.10 | 0.60 | 0.06 | 0.00 | 0.00 | 0.00 | 0.06 | 0.60 | 1.10 | 1.56 | 1.99 | 2.37 |
| 140 | 2.72 | 2.37 | 1.99 | 1.56 | 1.10 | 0.60 | 0.06 | 0.00 | 0.00 | 0.00 | 0.06 | 0.60 | 1.10 | 1.56 | 1.99 |
| 130 | 3.03 | 2.72 | 2.37 | 1.99 | 1.56 | 1.10 | 0.60 | 0.06 | 0.00 | 0.00 | 0.00 | 0.06 | 0.60 | 1.10 | 1.56 |
| 120 | 3.30 | 3.03 | 2.72 | 2.37 | 1.99 | 1.56 | 1.10 | 0.60 | 0.06 | 0.00 | 0.00 | 0.00 | 0.06 | 0.60 | 1.10 |
| 110 | 3.54 | 3.30 | 3.03 | 2.72 | 2.37 | 1.99 | 1.56 | 1.10 | 0.60 | 0.06 | 0.00 | 0.00 | 0.00 | 0.06 | 0.60 |
| 100 | 3.73 | 3.54 | 3.30 | 3.03 | 2.72 | 2.37 | 1.99 | 1.56 | 1.10 | 0.60 | 0.06 | 0.00 | 0.00 | 0.00 | 0.06 |
| 90 | 3.89 | 3.73 | 3.54 | 3.30 | 3.03 | 2.72 | 2.37 | 1.99 | 1.56 | 1.10 | 0.60 | 0.06 | 0.00 | 0.00 | 0.00 |
| 80 | 4.00 | 3.89 | 3.73 | 3.54 | 3.30 | 3.03 | 2.72 | 2.37 | 1.99 | 1.56 | 1.10 | 0.60 | 0.06 | 0.00 | 0.00 |
| 70 | 4.00 | 4.00 | 3.89 | 3.73 | 3.54 | 3.30 | 3.03 | 2.72 | 2.37 | 1.99 | 1.56 | 1.10 | 0.60 | 0.00 | 0.00 |

=MAX(0, -1.129 + 0.0633*[ABS(SBPCURRENT – SBP USUAL)] – 0.00019*[ABS(SBPCURRENT – SBP USUAL)]^2)

| Observation | Transf Supine -60deg tilt SBP diff | Transf Supine -60deg tilt RR diff |
|---|---|---|
| 1 | 0.4843 | 0.2479 |
| 2 | 0.9429 | 0.8005 |
| 3 | 0.4810 | 0.2395 |
| 4 | 0.1292 | 0.3320 |
| 5 | 0.2745 | 0.3927 |
| 6 | 0.4825 | 0.2068 |
| 7 | 0.2778 | 0.5222 |
| 8 | 0.9842 | 0.9939 |
| 9 | 0.2769 | 0.3214 |
| 10 | 0.1279 | 0.2659 |
| 11 | 0.6929 | 0.8677 |
| 12 | 0.4784 | 0.3026 |

FIG. 4

| Observation | Transf Supine -60deg tilt SBP diff | Transf Supine -60deg tilt RR diff |
|---|---|---|
| 1 | 0.5685 | 0.9762 |
| 2 | 0.0839 | 0.1268 |
| 3 | 0.5634 | 0.4598 |
| 4 | 0.9581 | 0.4598 |
| 5 | 0.3677 | 0.7450 |
| 6 | 0.8905 | 0.0557 |
| 7 | 0.1946 | 0.2189 |
| 8 | 0.8866 | 0.8472 |
| 9 | 0.3609 | 0.4265 |
| 10 | 0.5705 | 0.2273 |
| 11 | 0.0816 | 0.7450 |
| 12 | 0.3638 | 0.6260 |

FIG. 6

PREDICTING NEAR-TERM DETERIORATION OF HOSPITAL PATIENTS

CROSS-REFERENCE TO RELATED APPLICATIONS

This application is a continuation of, and claims priority from, U.S. patent application Ser. No. 13/270,748, filed Oct. 11, 2011, entitled "PREDICTING NEAR-TERM DETERIORATION OF HOSPITAL PATIENTS," which is incorporated herein by reference in its entirety.

BACKGROUND

Major problems in delivery of safe and effective care services in hospitals involve deficiencies in the quality and continuity of patient care, including the monitoring of each patient's condition over time. Despite recent advances in electronic health records (EHR) systems, the present state of the art in medical care within hospitals still does not in general utilize the accruing medical record information for active, prognostic use-cases, to predict the future status or events or outcomes that are likely to materialize for the patient. Instead, in many scenarios the EHR acts mainly as a passive repository for documenting and storing the information that is generated by each provider and each department, which characterizes the current or previous status or outcomes that have already materialized.

During a typical hospital stay, each patient may see many doctors and many nurses. Such fragmentation of responsibility for the care process challenges the ability of each provider to quickly and accurately grasp the meaning of the constellation of accumulating clinical and laboratory facts about the patient, to understand trends that may be developing in the patient's health status, and to evaluate the urgency of attention that is necessary to effectively address existing or newly developing issues or to successfully prevent potential adverse events and complications.

The consequence of the proliferation of medical information in each patient acute care episode, combined with the all-too-common fragmentation of the care process with responsibilities divided among dozens of provider personnel most of whom do not have deep or longstanding familiarity with the patient, is that unexpected physiologic deterioration occurs to many patients, especially post-operatively or post-medical procedures, such that a medical crisis ensues. Precious care resources of the hospital are diverted in an attempt to save the patient, and needless suffering and even death occur. In many such instances, the impending deterioration could have been predicted—provided that enough vital signs and other monitoring data were acquired in advance; provided that that data were integrated into a suitably accurate personalized predictive model; and provided that the output of the model were effectively communicated to the providers who have the responsibility to intervene and prevent or manage the predicted risk of acute deterioration.

While the recognition and interpretation of some acute events such as loss of consciousness or dyspnea or new onset of fever or decompensation of blood pressure or other hemodynamic parameters are clear-cut, in other cases the events or changes are not readily recognized or interpreted, particularly by personnel who have not previously been involved in the patient's care. A change in systolic blood pressure (SBP) to 180 mm Hg might for one person be of ominous and critical significance (for example, in a person whose usual SBP is 110 mm Hg), but carries no adverse prognostic significance for a person whose chronic, poorly controlled hypertension is associated with a usual SBP of 190 mm Hg.

Life-threatening deterioration of patients' health status while in a hospital is often preceded by abnormalities in hemodynamic variables and organ-system parameters measured by clinical and laboratory tests. Over the past several years there have emerged a variety of rapid response team (RRT) and early-warning system (EWS, MEWS, PARS, etc.) methods that aim to combine such information and calculate an index or score that can be used to gauge the risk of acute deterioration and, if the risk is sufficiently high, notify the responsible physicians, transfer the patient to an alternate location where intensified monitoring and care services can be provided, and/or undertake other actions to prevent or mitigate the predicted deterioration.

Frequently, however, there is no obvious or apparent abnormality in vital signs or other clinical or laboratory variables that precedes the deterioration and, in such instances, the RRT- and MEWS-type calculations fail, giving a 'false-negative' assurance that there will be no near-term deterioration in the patient's status when in fact deterioration does materialize. A Hodgetts Score=7 has only a sensitivity of 64%, and Score=8 yields sensitivity of only 52%, for example. In other words, in 36% and 48% of cases, respectively, a false-negative interpretation is ascribed and the Hodgetts score fails to alert the caregivers to the deterioration that ensues.

In other instances, fluctuations in the values of physiologic variables that are utilized by an RRT or MEWS-type calculations give rise to 'false-positive' alarms, incorrectly identifying a given patient as one in whom acute deterioration is likely when in fact no deterioration occurs. In such a situation, valuable resources associated with intensified monitoring or other interventions are misapplied. The resources are allocated to the given patient, in whom those resources are not in fact necessary and provide no benefit, and, insofar as resources are finite and in short supply, those resources are during that same time interval withheld from other patients, for whom the resources might have provided greater value and benefit.

Thus, a significant limitation of a number of existing models for determining or predicting patient deterioration in health is of limited statistical sensitivity and specificity, with substantial false-negative and false-positive rates. Most of the commonly applied regression equations or CART or decision-tree or neural-network or other classification algorithms are able only to achieve receiver operating characteristic (ROC) area-under-the-curve (AUC) discrimination performance of approximately 75% to 80%. Certain existing models achieve ROC AUC of up to 90% in selected subpopulations, such as patients in an emergency department.

Another significant limitation looking at the current state of the art is that the variables that are included in the predictions are often temporally 'lagging indicators' (such as serum creatinine or other metabolic indicators of kidney function), which broadly characterize a background of diminished organ-system capacity or organ-system vulnerability to physiologic stressors. But it is a background that is at the time of calculation of the RRT- or MEWS-type score already obvious to the physicians who are managing the patient's care. The RRT- or MEWS-type score does not tell the physicians anything that they do not already know. The same is also true for variables that are not temporally 'lagging' ones.

For example, 'threatened airway' (or 'respiratory rate <5 bpm or >30 bpm') is included in several models of the prior art, but this is not a variable that should require elaborate calculations to interpret, nor should decision-making regarding whether to intervene or intensify monitoring of the patient await computation of a multivariable score that incorporates such variables.

An acute change in mental status (such as is often measured by Glasgow Coma Score or other scales) is likewise intuitively obvious with regard to portending increased risk of further deterioration or adverse events. An acute change in body temperature is another example of a self-evident or 'obvious' indication of acutely altered risk of acute deterioration. The risk that is entailed by such information is obvious on its face, and an index or score that references these variables adds little value toward prediction or anticipatory decision-making to prevent declining health or to manage adverse events that have not thus far materialized. Such 'obvious' information and scores derived from them primarily serve (a) as a post-facto form of concise documentation of the materialized abnormalities and associated, already-obvious increased risk and (b) as a means of triaging or prioritizing patients according to already-materialized severity of illness.

Still further, another limitation of the existing art is that the predictive models typically rely upon measurements that are often performed in an imprecise and inconsistent manner. For example, measurement of diastolic blood pressure (DBP) by auscultation of Korotkoff sounds with a stethoscope and blood pressure cuff ought in principle to be a relatively accurate and precise process. However, haste and poor technique on the part of the observer often cause DBP measurements to be in error by many millimeters of mercury. It is difficult to compel improvements by busy caregivers who are prone to make imprecise and inconsistent measurements. As a result, any point-estimate or single-point-in-time predictor that is based on variables whose values tend to be subject to inaccuracy, imprecision and inconsistency in measurement technique tend to generate wide variations in predicted risk. By contrast, variables whose measurements do not present such difficulties (such as systolic blood pressure SBP and heart rate HR) are amenable to more accurate, precise predictions.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

A system, method and computer-readable media are provided for determining a numerical probability of acute deterioration in hospitalized patients. Serial medical data of a particular patient is received from a plurality of inputs. Based on a transformation of the data, a predicted probability of acute deterioration (PPOD) score is calculated. The PPOD score is displayed for clinicians, to ensure that timely and effective measures may be taken to mitigate the patient's chances of acute deterioration.

BRIEF DESCRIPTION OF THE DRAWINGS

The present invention is described in detail below with reference to the attached drawing figures, wherein:

FIG. 3 is a table showing indices of the deviation of a current systolic blood pressure (SBP) from a patient's usual SBB, computed as a quadratic function of the absolute value of the difference between the current SBP and the patient's usual SBP;

FIG. 4 shows results corresponding to a patient whose condition deteriorated within 18 hours;

FIG. 6 shows results corresponding to a patient whose condition did not deteriorate.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention relate to determining a numerical probability of acute deterioration in hospitalized patients. In embodiments, serial medical data of a particular patient is received from a plurality of inputs. Based on a transformation of the data, a predicted probability of acute deterioration (PPOD) score is calculated. The present invention is particular beneficial for patients in whom other acute condition or deterioration scoring systems yield false-negative results. Despite the superior sensitivity to accurately recognize patients at-risk whose abnormalities are not obvious, the invention simultaneously achieves specificity that is superior to the prior art. In an embodiment, the ROC AUC of the present invention is greater than 89% in a sample patient population. In part, this greater accuracy and discriminatory power to classify individual cases correctly is due to the invention's utilization of multivariate copula timeseries methods, which enable inferences based on statistical interrelationships between two or more clinical or laboratory variables measured simultaneously at a plurality of timepoints.

In embodiments, the present invention receives incoming medical data from a patient (e.g., through an interface), transforms the medical datum into a transformed PPOD value, and combines the transformed PPOD values corresponding to each of the medical datum into a single PPOD value. The predicted probability of acute deterioration (PPOD) score may then be displayed on a computing device as a PPOD plot over a predetermined time frame, such that a user may identify risk trends in a patient by evaluating said PPOD plot.

In addition to the features of the predicted probability of acute deterioration and uses thereof, it is further contemplated that a plurality of PPOD scores of various patients relevant to a clinician (provider) or a hospital or practice area may be assembled as a panel of predicted probability of acute deterioration charts, giving a nurse or doctor an overview as to the progress of many patients at one time.

Figure 1:
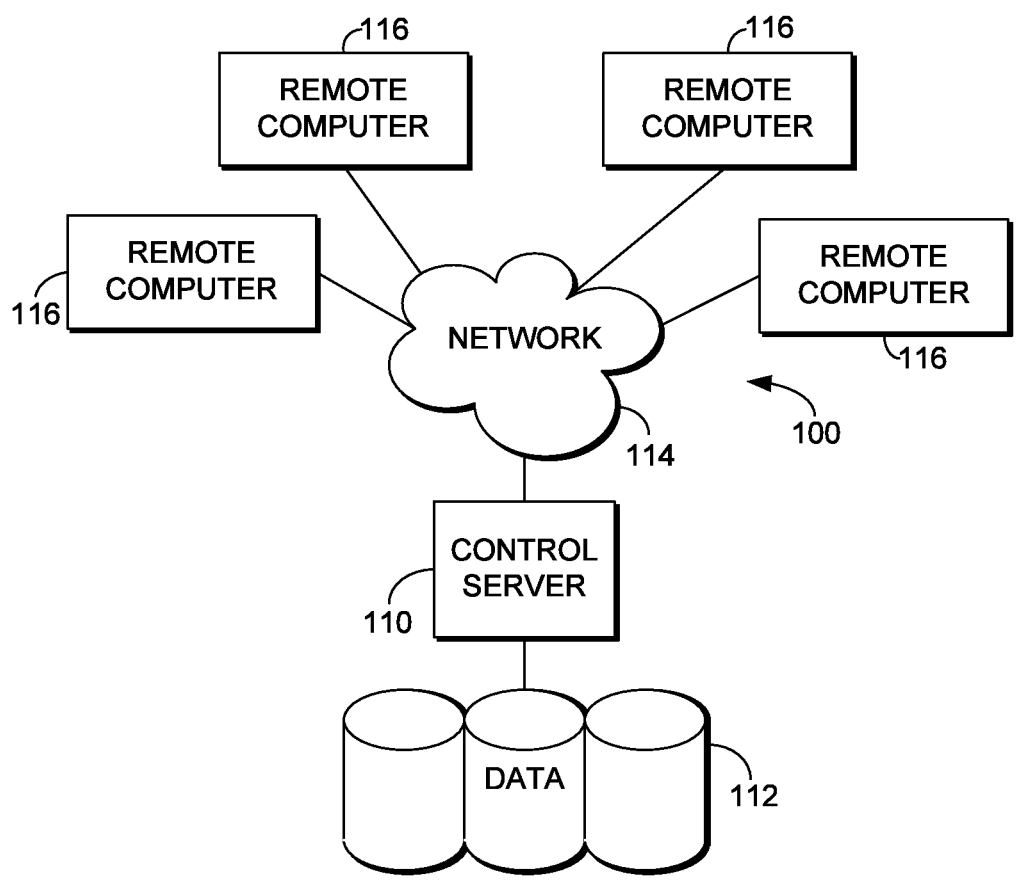
FIG. 1 is a block diagram of an exemplary computing environment suitable for use in implementing the present invention.

Having briefly described embodiments of the present invention, an exemplary operating environment suitable for use in implementing embodiments of the present invention is described below. Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network.

Remote computers 116 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 116 may also be physically located in nontraditional medical care environments so that the entire healthcare community may be capable of integration on the network. The remote computers 116 may be personal computers, servers, routers, network PCs, peer devices, other common network nodes, or the like, and may include some or all of the components described above in relation to the server 110. The devices can be personal digital assistants, mobile phones, tablet computers, or other like devices.

Exemplary computer networks 114 may include, without limitation, local area networks (LANs) and/or wide area networks (WANs). Such networking environments are commonplace in offices, enterprise-wide computer networks, intranets, and the Internet. When utilized in a WAN networking environment, the server 110 may include a modem or other means for establishing communications over the WAN, such as the Internet. In a networked environment, program modules or portions thereof may be stored in the server 110, in the database cluster 112, or on any of the remote computers 116.

For example, and not by way of limitation, various application programs may reside on the memory associated with any one or more of the remote computers 116. It will be appreciated by those of ordinary skill in the art that the network connections shown are exemplary and other means of establishing a communications link between the computers (e.g., server 110 and remote computers 116) may be utilized.

In operation, a user may enter commands and information into the server 110 or convey the commands and information to the server 110 via one or more of the remote computers 116 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 110. In addition to a monitor, the server 110 and/or remote computers 116 may include other peripheral output devices, such as speakers and a printer.

Although many other internal components of the server 110 and the remote computers 116 are not shown, those of ordinary skill in the art will appreciate that such components and their interconnection are well known. Accordingly, additional details concerning the internal construction of the server 110 and the remote computers 116 are not further disclosed herein.

Various patient deterioration early-warning systems (e.g., EWS, MEWS, PARS) are typically used to determine a patient's need to be transferred to the ICU by providing an emergency 'alert' notification via email or SMS text message or by other means, to the attending physician and to Rapid Response Team staff, who then undertake appropriate review and decisions as indicated. However, many existing RRT- and EWS-type systems are point-estimate predictions at a point in time and do not convey longitudinal trend information. Also, they are limited in the number of factors analyzed and thus are quite insensitive to a broad range of health conditions that account for a substantial proportion of the deterioration events that arise.

For example, a patient whose heart rhythm is prone to become rapid (nonsustained ventricular tachycardia; NSVT) may be at risk for life-threatening cardiac arrhythmias. In many such patients, the body's circulatory system has sufficient hemodynamic reserve and resiliency to tolerate NSVT for extended periods of time. But in other patients, the hemodynamic reserve may be deficient, or the baroreceptor response sensitivity may be impaired, or other abnormalities may exist such that NSVT is poorly tolerated even briefly, producing a cascade of interrelated cardiac ejection and conduction derangements, leading to life-threatening cardiac events. None of the prior art RRT- or EWS-type systems collect or analyze variables so as to be able to ascertain the ability to tolerate NSVT or other transient stresses.

Derangements in vital sign measurements may presage inadequate tissue oxygenation and/or reduced ability to tolerate ventricular tachycardia or other acute conditions, which in turn can lead to multi-organ dysfunction and an increase in the risk of death. Early detection of physiologic derangements may lead to more timely treatment, less organ dysfunction and reduced risk of death. But early detection cannot occur unless vital signs and other variables are measured sufficiently frequently. Frequent measurement is a strategy that has often been neglected but is now progressively improving since the introduction of RRT- and MEWS-type systems.

Parasympathetic and sympathetic nervous system disturbances are found in many conditions, including advanced age, ischemic heart disease, heart failure, and autoimmune conditions, among others. In various systemic diseases, such as diabetes mellitus, reduction of heart rate (HR) variability typically precedes the clinical expression of autonomic neuropathy. Spectral analysis of HR variability is a sensitive, non-invasive tool to detect early disturbances of the autonomic nervous system.

The baroreceptors in the carotid sinus and the baroreflex feedback loop constitute a primary physiological system involved in short-term blood pressure control. Stretch receptors in the carotid sinus and aortic arch are stimulated by the distension which accompanies increased blood pressure, impulses pass via afferent nerves to vasomotor and cardioinhibitory centers in the brainstem resulting in vasodilatation, bradycardia, and reduction in cardiac output. Conversely, decreased blood pressure is sensed by the baroreceptors resulting in cardiostimulation and vasoconstriction, tachycardia, and increase in cardiac output. Blunted baroreflex sensitivity is associated with increased risk of vasovagal syncope, orthostatic hypotension, and sudden cardiac death following myocardial infarction.

Orthostatic challenge to baroreceptor reflex sensitivity (BRS) in patients who are at high risk of acute deterioration frequently induces the following significant effects: a greater-than-normal increase in HR (a disproportionately large decrease in mean interbeat interval (IBI) in milliseconds), an increase in the mid-frequency band log-power of HR, a decrease in the high-frequency band log-power of HR, an increase in systolic blood pressure (SBP), an increase in the variation coefficient SBP, an increase in the mid-frequency band log-power of SBP, an increase in diastolic blood pressure (DBP), an increase in the variation coefficient DBP, and a decrease in the BRS index of the mid-frequency band.

Measuring these variables ordinarily requires repeated electrocardiography and relatively complicated frequency-domain spectral analysis computations. However, the studies resulting in the present invention revealed that even simple serial vital signs measurements are able to detect changes in BRS and autonomic physiology IBI-SBP relationships, so long as sufficiently many longitudinal observations of supine- and 60-degree-tilted HR and SBP are acquired and suitable tie-breaking transformation and probit transformation of IBI and SBP differences and logarithmic transformations of the estimated baroreceptor reflex sensitivity (BRS) are performed.

A significant orthostatic pressure challenge is easy to arrange in routine patient care settings. First, the patient is placed in a supine position in bed and the resting HR and SBP are measured, either manually or by automated monitoring equipment. Then the motorized patient bed is elevated to an angle of 60-degrees, and the HR and SBP are again measured within 1 to 2 minutes after elevation of the patient seated upright in the 60-degree bed. In one preferred arrangement, a total of at least 12 such pairs of supine and 60-degree measurements are collected, over a period of not less than 6 hours.

Embodiments of the present invention employ a copula analysis that measures the statistical dependency (or lack thereof) between two timeseries, namely, a timeseries of supine vs. 60-degree tilt differences in mean interbeat interval (IBI, or electrocardiogram R-to-R interval) and a timeseries of supine vs. 60-degree tilt differences in SBP. The comparison of supine vs. 60-degree tilt measurements is a low-risk, low-cost, noninvasive way to challenge the patient's autonomic nervous system that controls vascular tone and thereby estimate the baroreceptor response sensitivity (BRS). If the BRS is decreased compared to normal, the patient's physiologic ability to withstand hemodynamic and cardiac stresses is likely impaired, in a manner that is strongly associated with acute deterioration. Moreover, and even if BRS is still within the normal range, if the statistical copula between the IBI and SBP supine vs. 60-degree tilt differences displays a bivariate dependency and is well-fit by an extreme-value distribution (e.g., Gumbel distribution), that too is a strong correlate of subsequent acute deterioration. Computation of the BRS and of IBI-SBP copula as part of the present invention thereby reveals physiologic properties that are otherwise not evident in the raw data.

There are some deterioration events that are acute, with sudden onset and no apparent antecedent abnormality or multivariate cluster of abnormalities that predict the imminent event. Fortunately from the screening and diagnostic perspective, a majority of patients who deteriorate have a prodrome of hemodynamic and other abnormalities for many hours in advance of the onset of acute deterioration. This affords a 'window of opportunity' sufficient for undertaking effective preventive and corrective actions and intensified monitoring so as to intervene more quickly and effectively than would otherwise tend to occur.

In many instances, the prodrome involves a change in the bivariate statistical relationship (copula) of the heart RR interval difference vs. the systolic blood pressure difference that is associated with an autonomic challenge, such as elevating the patient's position from supine to 60-degree elevation in bed or infusion of 4 mcg/kg of epinephrine or phenylephrine. A normal patient who is not at risk of deteriorating tends to have a copula that is well-fit by a bivariate normal distribution, but a patient who is destined to deteriorate frequently has a copula that is a member of the family of extreme-value distributions, such as Gumbel distribution.

The practical reality, however, is that statistical tests of the goodness-of-fit of distributions to data require a considerable number of observations in order to produce a reliable conclusion or p-value. In an exemplary embodiment of the present invention, the model development dataset and model validation dataset were able to generate stable, reliable p-values only for copulas consisting of 12 or more sets of measurements pre- and post-challenge. Accordingly, embodiments of the present invention achieve superior predictive accuracy and statistical discrimination by (a) arranging suitable repeated challenge to the body's autonomic nervous system and collecting heart rate and blood pressure data before and after each such challenge, and (b) processing the resulting array of information so as to generate a predicted probability of acute deterioration (PPOD) from the log-transformed baroreflex sensitivity, from the index of systolic blood pressure (SBP) deviation from the patient's usual SBP, and from the copula of probit-transformed pre- and post-challenge interbeat interval (IBI) difference and pre- and post-challenge SBP difference values.

In embodiments, the present invention finds significantly higher supine vs. 60-degree SBP differences, significantly lower log(BRS), and significantly lower values of the modulus between SBP and IBI, as an indicator of the BRS, during tilt in patients who deteriorate as compared with healthier controls who did not deteriorate acutely. The present invention further finds that the bivariate copula of IBI vs. SBP differences of patients who deteriorate are well-fitted by Gumbel or other extreme-value copulas, showing a high degree of interdependency between IBI difference and SBP difference associated with autonomic (orthostatic 60-deg tilt) challenge.

By contrast, the bivariate copula of healthier patients who do not deteriorate are well-fitted by the normal copula or the Frank copula, showing IBI and SBP differences to be relatively independent of each other statistically under conditions of autonomic challenge.

The natural logarithm of the mean baroreceptor reflex sensitivity (BRS) obtained over a series of not less than 12 such measurements, the index of the deviation of the patient's current systolic blood pressure from the pressure that is usual for the patient, and the probability p>0.10 that the bivariate copula of the autonomically challenged vs. unchallenged heart rate difference timeseries and the autonomically challenged vs. unchallenged systolic blood pressure difference timeseries is not different from an extreme-value copula are combined to create a statistical classifier. In one embodiment these three variables are combined via a logistic regression equation to produce a predicted probability of acute deterioration (PPOD). Other embodiments may utilize alternative variable-combining algorithms and equations (such as neural-network, CART classification and regression tree, decision-rules, support-vector machine algorithms, etc.) to achieve a comparable classification or predicted probability.

Computation of Risk of Acute Deterioration

Copulas are a way of quantitatively characterizing the mutual and joint statistical dependence structures of vectors of multiple random variables. Although copulas have been studied for decades, they were not extensively applied until relatively recently. Interest in copulas has been renewed recently in biostatistics, reliability engineering, and financial engineering, and other fields.

Modeling multivariate longitudinal data is an important challenge in biostatistics. In the literature, most of the time the considered models assume that the original data or some transformation of them are multivariate normal with a variance-covariance matrix structured to describe serial dependence, heterogeneity and dependence between response variables. Unfortunately, normality is certainly not a rule in practice, particularly with physiologic variables. When the responses are not normally distributed, and when their marginal distributions are not in the same family, alternatives to the multivariate normal must be found.

Very few tools exist in the literature to model such data. Zeger and Liang consider, at each time point t, a model for the mean of each outcome conditional on its history and on the values of the other outcomes at time t. The conditional variance of each outcome is assumed proportional to a fixed function of the conditional mean.

More tools can be found in the literature to deal with data of mixed types when the vectors of observations are only observed once on independent or clustered units. A joint model for mixed continuous and categorical data was first proposed by Olkin and Tate. It was extended to deal with missing values in reference. Conditionally on the categorical responses combination (with a marginal multinomial distribution), they assume that the continuous variables are multivariate normal. The EM algorithm is used to obtain the maximum likelihood estimators (MLEs) in the presence of missing values. Liu and Rubin generalized the approach by considering a multivariate t distribution instead of the more constraining multivariate normal and by allowing different covariance matrices across cells.

Many models for mixed type data can be found in the literature devoted to the analysis of toxicity studies. These usually involve clustered responses of mixed types. One example is in toxicology. Fitzmaurice and Laird proposed modeling such data using marginal regression models for each of the responses while treating the intracluster correlation as a nuisance factor. GEEs are derived to obtain consistent parameter estimates while accounting for intracluster correlation. The parameters from the marginal regression models are robust to dependence misspecification.

In embodiments of the present invention, the binary "deteriorated" vs. "did not deteriorate" response is modeled as an unknown copula class of supine and 60-degree tilt IBI difference values and supine and 60-degree tilt SBP difference values. Patients who do not deteriorate acutely tend to have copulas that are bivariate normally distributed, while patients who do deteriorate empirically tend to have copulas that exhibit dependency that is characteristic of an extreme-value (Gumbel) copula. The physiologic reasons why this is so require further study. However, the statistical association of the "deteriorated" response with the extreme-value copula dependence structure may be empirically utilized in a predictive model regardless whether the mechanism that underlies the association is elucidated. Likely, the mechanism leading to the extreme-value copula dependence between IBI difference and SBP difference under conditions of autonomic challenge has to do with altered sympathetic and/or parasympathetic vascular tone or with acute alteration of baroreflex sensitivity and consequent acutely altered hemodynamic compensatory capacity.

In some embodiments, a single term in the predicted probability of acute deterioration formula may contain multiple medical data inputs. For example, as noted in the above incorporated discussions of PPOD various medical readings (supine and 60-degree tilted SBPs, IBIs, etc.) are each transformed before fitting a 12-point copula and calculating the PPOD value. It is understood however, the multiple medical data inputs may be combined before being transformed, such that the transformed numbers used for forming a portion of the PPOD, are a combination of multiple health readings.

Regan and Catalano showed how to build a joint model for clustered binary and continuous outcomes with an application to developmental toxicology. They use an extension of the correlated probit model to obtain a joint distribution for the binary and the continuous responses. A joint multivariate normal distribution is considered for the corresponding latent variables and each outcome is analyzed with a marginal dose-response model. The covariance matrix takes into account the correlation between outcomes and the correlation due to clustering. This is an important improvement of references and as model estimates of the correlation between responses and the evolution of these correlations with dose are available. A marginal approach was preferred to conditional models with the arguments that the biological mechanism relating the chemical exposition to developmental problems is not well understood, and that conditional models are difficult to use to quantify risk or to study the marginal effect of dose on an isolated response.

In embodiments of the present invention, copulas are used to model multivariate non-normal longitudinal data. By definition, an n-dimensional copula is a cumulative distribution function with uniform marginals. In the present invention, the three responses were treated as if they were multivariate continuous although the heart rate and blood pressure are integer-valued and essentially discrete. When measured manually, the heart rate is often quantized into discrete values modulo-4, inasmuch as heart beats are typically observed for 15 seconds and multiplied by 4 to obtain the minute-wise heart rate. When blood pressure is measured manually, the pressures are typically recorded in even numbered increments, modulo-2, due to the nature of the sphygmomanometer gauge or quantization of digital display values. These data-conditioning considerations necessitate certain preprocessing to enable the copulas for PPOD calculations to be numerically stable. Copulas can be used whatever the type and the marginal distribution of the involved variables, but when non-continuous variables are involved, one must use finite differences instead of analytical derivatives of the copula to calculate the likelihood values and one must randomly perturb the data values to break ties. In the preferred embodiment, this is done by randomly adding or subtracting a small value from each supine vs. 60-degree-tilt IBI difference and from each SBP difference.

The data of relatively healthy patients who do not deteriorate are usually well-fit by the normal copula or by the Frank copula. Indeed, by specifying two correlation matrices (which should be named more generally dependence matrices), we have defined entirely the dependence arising due to the repeated character of our measurements with the first copula and the dependence between the different types of measurements at each time point with the second copula. However, nothing prevents us from using copulas other than the normal one. We refer the interested reader to references for alternative multivariate copulas.

Except when considering bivariate Archimedian copulas, descriptive and graphical tools are clearly lacking to understand the dependence structure in the data and to make a preselection of appropriate copulas. This is the subject of ongoing work that we plan to publish later. For the moment, we select our copula(s) in simple parametric families (indexed by one or two parameters) by taking the one giving the largest log-likelihood.

The estimation of the parameters (from the second copula) describing the dependence between the different variables was made conditionally on the fitted univariate marginal distributions. This uses the argument that continuous margins in a copula model do not depend on the choice of the dependence structure of the data, suggesting that the modeling and the parameter estimations for the margins and the copula can be made separately.

In embodiments of the present invention, the bivariate copula of (a) the interbeat interval (IBI) difference calculated from supine and 60-degree tilt heart rate measurements and (b) the supine vs. 60-degree tilt systolic blood pressure (SBP) difference frequently exhibits properties of extreme-value copula (Gumbel copula) dependency and distribution structure in patients who subsequently deteriorate with in an acute period of less than 24 hours, whereas the IBI-SBP difference copula of patients who do not deteriorate shows little dependency between the variables' distributions. The copulas may in principle be of any dimension, but in the preferred embodiment involve not less than 12 contemporaneous IBI and SBP supine and 60-degree tilt values separated by not less than 30 min. In the preferred distributed client-server embodiment, an indexing service indexes and maintains buffered (cached) copies of the most recent 12 such sets of values for each applicable hospital inpatient, as well as a cached copy of the usual SBP for each applicable patient, for use in subsequent PPOD computations.

In a set of studies conducted, the copulas of stable non-deteriorating patients are well-fitted by the normal copula or the Frank copula. To insure numerical stability of rank-based copula analytics, the raw values are first perturbed so as to eliminate any 'tied' values by adding or subtracting a small fractional (<0.1) random value from each vector element before forming the bivariate copula of the vectors.

The presence of ties in the data substantially affects the estimation of the p-value. Ignoring the ties, by using midranks to compute pseudo-observations or by other methods, can likewise bias the estimate of the p-value. Kojadinovic and Yan recommend constructing pseudo-observations by randomly breaking the ties, shifting the tied ordinates and abscissas by small random amounts, which is a methodology employed in an illustrative embodiment of the present invention.

As previously mentioned, embodiments of the present invention involve statistical testing to determine whether or not the copula of a particular patient is or is not an extreme-value copula, comparing the empirical copula with a rank-based nonparametric estimator of the patient's copula derived under Pickands-type extreme-value dependence. The value of a binomial variable denoting the extreme-value copula predicate may be generated by a variety of computational methods. In an illustrative embodiment, the PPOD inference engine service calls an evTestA function in the open-source R statistical package with multiplier iterations count of at not less than 1,000. The determination of extreme-value dependence structure, as is done in the illustrative embodiment by the R evTestA function, returns the test statistic and the p-value of the test statistic. If the p-value is greater than 0.1, the extreme-value copula predicate value is set equal to 1. Otherwise, it is set to zero. The value of the extreme-value copula predicate variable is one of three variables that is employed in calculating the PPOD probability. The second of the three variables, the natural logarithm of the mean baroreflex sensitivity [ln(mean(BRS)), in log msec/mmHg], is computed from the same array of supine and 60-degree tilt IBI and SBP measurements. The third of the three variables, the index of the deviation of the current SBP from the patient's usual SBP (shown in the table of FIG. 3), is computed as a quadratic function of the absolute value of the difference between the current SBP and the patient's usual SBP.

In an illustrative client-server embodiment, the PPOD probability is calculated via a logistic regression equation (shown as Eq. 1, below) in which the values of these three variables appear as terms:

$$PPOD = \exp(6.206 - 3.076 * \ln BRS + 7.644 * SBPscore + 3.194 * evTestAp)/(1 + \exp(6.206 - 3.076 * \ln BRS + 7.644 * SBPscore + 3.194 * evTestAp)) \quad \text{Eq. 1:}$$

and the resulting PPOD value is returned (a) to the inference engine whose rules and processes may undertake realtime notification of responsible physicians and nurses via email, SMS text message, or other appropriate means of notification, and (b) to the calling client application program for display to the clinician user or for trend plotting or other uses. The PPOD threshold at which notification alerts are emitted may be selected at the health care organization's (e.g., hospital's) discretion, depending on the epidemiology of acute deterioration incidence rates, staffing levels of clinician individuals able to respond to such notifications, and other factors, as those skilled in the art will appreciate. In one embodiment, the threshold for notification is PPOD>0.50.

Recalibration of Eq. 1 may be necessary for patient populations that differ substantially from the populations whose study led to the present invention. The PPOD as disclosed in the incorporated documents, and above may optionally be recalibrated to each hospital in which it is implemented. Most hospitals have slight differences in procedures, standards, requirements and other elements of daily practice as compared to other hospitals and some embodiments of the present invention may be adapted to a specific hospital's preferences. By adjusting the PPOD equation according to an individual hospital's procedures, staffing, and patient population, the PPOD may be more accurate.

The process for performing such recalibration will be familiar to those practiced in the art and involves accumulation a prospective observational cohort of a sufficient number of patients, both cases who acutely deteriorated and controls who did not, and the supine and 60-degree tilt IBI and SBP data from each. In an illustrative embodiment, multivariate logistic regression is performed on a randomized subset of such data, to calculate localized values of the intercept and the coefficient for each of the three variables. Then the other cases and controls that were not included in the first randomized subset are utilized as a confirmatory 'validation' subset and logistic regression is performed on these. If the intercepts and coefficients are in substantial agreement in the 'model development' and 'model validation' regressions, then the new localized model is accepted and its values replace the default values in the PPOD equation. If the intercepts and coefficients are discordant, then the process of accumulating additional cases and controls continues.

Figure 5:
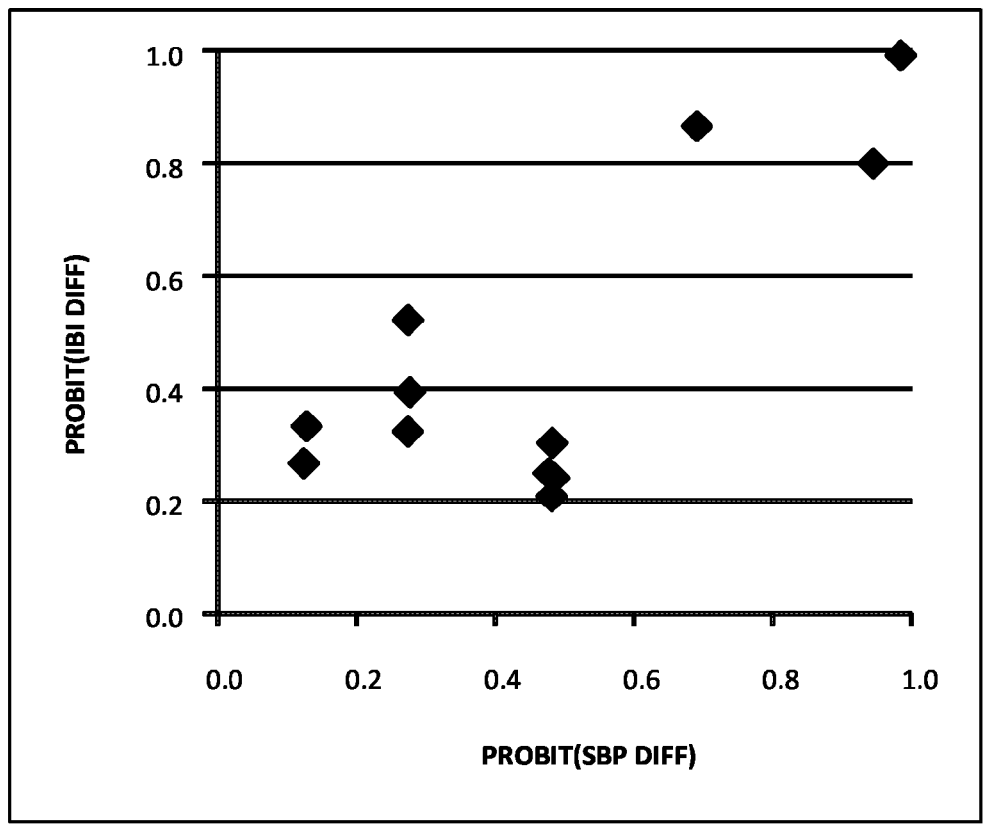
FIG. 5 shows a plot of the results in of the table of FIG. 4.

Patient whose condition deteriorated within 18 hours (see FIGS. 4 and 5)

Figure 7:
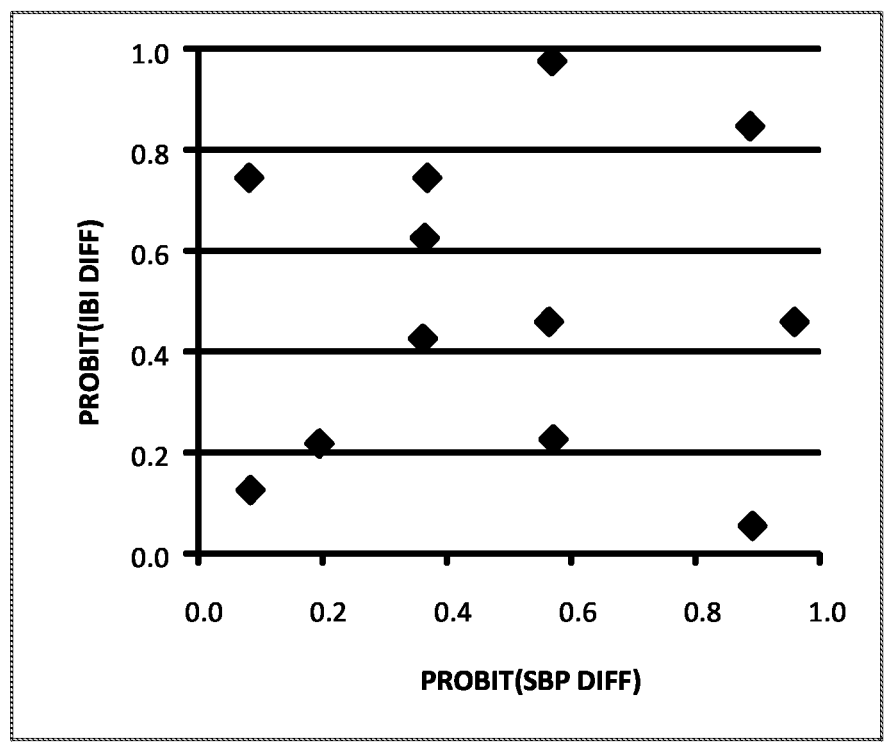
FIG. 7 shows a plot of the results in of the table of FIG. 6.

Patient whose condition did not deteriorate (see FIGS. 6 and 7)

The monitoring of a clinically unstable patient must be associated with an appropriate treatment to improve care, which can only occur following an appropriate medical review triggered by a meaningful communication by the bedside nurse to physician.

In one embodiment, the Predicted probability of acute deterioration may be used to predict the odds of a crisis within N number of hours. Consider, for example, there is a 50% chance of a crisis in the next 12-24 hours. This information may be used to assign additional observation to particular patients, or if a crisis is judged to be imminent, a call may be initiated to a Rapid Response Team. Another use for the Predicted probability of acute deterioration is to route doctor's rounds, so that walking instructions can be provided for a doctor doing rounds. This will allow a doctor to quickly attend to patients requiring more attention first, and then proceed to patients whose condition is less urgent.

In some embodiments, creating the standard curve may entail reviewing graphs of all previous patients with the same DRG/IDC-9 code in a database and plotting them as one or more curves. The curve may be represented by an average curve, all of the individual patient's curves, a median curve, a top $25^{th}$ percentile and a bottom $25^{th}$ percentile, plus or minus some number of standard deviations thereby creating a normative recovery as well as upper and lower bounds, any combination of the foregoing or any other representative indicator as not all embodiments of the present invention are intended to be limited in this respect. By using these types of normative curves a doctor may be able to see that even if a patient is recovering, the patient might be recovering more slowly than the average patient with a similar condition and this slower recovery might be cause for further investigation.

Not only may the grouping codes be useful in comparison with the predicted probability of acute deterioration, but the grouping codes may be utilized in generating a more accurate predicted probability of acute deterioration. In some embodiments, a user may modify the algorithm used to generate the predicted probability of acute deterioration based on the diagnosis or grouping code of the patient in order to have the predicted probability of acute deterioration more accurately reflect the patient's recovery.

Yet another exemplary use of the PPOD arrangement is its use in predicting the length of stay for a patient or group of patients, sometimes termed ELOS (expected length of stay). Such an arrangement may be used to apply to a group of patients and therefore allowing a hospital to create a forward-looking resource plan, i.e. how many nurses are needed on a subsequent day of the week based on the current hospital population in a particular department. Some grouping codes, such as DRG, have ELOS times built into the grouping code, such that someone having a certain surgery will have an ELOS of a certain amount of time.

By comparing a patient's PPOD value with a standard, many inferences may be drawn from the comparison. For example, in some embodiments, patients may be given a category, such as critical, critical but stable, serious, serious but stable, fair, and/or good. These categories may be words or terms, numbers (such as "low risk", "intermediate risk", "high risk", "very high risk" or 1 to 4), colors (such as a heat-map display comprised of red, orange, yellow, and green shading of PPOD values), a system of categorizing, or other appropriate information display system. In addition, the categories may be discrete, such as choosing one of four colors, or they may be continuous.

By having patients categorized, administrative decisions and care priority can be determined accordingly. For example, in some embodiments, a nurse scheduling tool may be incorporated or separately determined which would allow shift nurses to see the conditions of all patients on the floor and assign nurses based on skill level, so that more experienced nurses have more critical patients and newer nurses have more stable patients. In some embodiments, the nurse scheduling tool may rank patients, for example, 1-10 and allocate patients to each nurse so that no nurse has a total patient rank of for example, more than 25 (e.g., two very critical patients of rank 10 and one fair but stable patient of rank 5, four fair but stable patients of ranks 5.2, 5.4, 5.7 and 6.1, or two serious patients of rank 8 and one serious but stable patient of rank 7.2). Similarly, these systems may be applied to routing a doctor's rounds, as described above.

In some embodiments, the PPOD may be used for evaluation purposes. For example, the PPOD may be used to evaluate the performance of a particular doctor's or nurse's performance, or even of the hospital itself. It can also be used to evaluate a particular treatment by studying PPOD charts of patients that underwent a particular treatment.

In addition to evaluation of doctors, the system may be used to compare effectiveness of medical treatments, compare the quality of care provided by different wards or hospitals, and compare the skill of healthcare providers by providing an objective assessment of a patient's health and response to various factors. In some embodiments, the algorithm may be customized after a patient's stay to further evaluate the care of the patient and compare the patient with other patients. For example, if two patients had the same diagnosis and received different treatments, a hospital or doctor may want to compare those two patients' recoveries. Any two patients are evaluated using the same PPOD algorithm, but the comparison is tailored to focus on the recovery from the treatments and exclude unrelated deviations.

In another embodiment, the predicted probability of acute deterioration chart shapes can be clustered to discover the "types" of patient health trajectories. General prototypical trajectories, or trajectories computed as a function of disease or procedure may be compared against actual PPOD charts to determine how a particular patient is responding to treatment. Once a predicted probability of acute deterioration chart is assigned to such a prototypical trajectory, it may further indicate the likelihood of various outcomes. In some embodiments, this may be accomplished by using DRG/IRC-9 groupings.

In another embodiment of the present invention, the PPOD may be used as part of a remote monitoring service, where a remote web-based health service provider can monitor the score of several patients and alert an on-site staff if there is an emergent condition meriting their attention. The PPOD can be calculated using logistic regression equations, neural networks, or other analytical methods. The predicted probability of acute deterioration values may be fed to a cloud-based healthbank or a multi-institution central data hub and be used to monitor for large scale trends in health problems, including a bioterrorism or other public health occurrences.

While in some embodiments an individual predicted probability of acute deterioration falling below a minimum mark or the change in predicted probability of acute deterioration or slope of the timeseries of predicted probability of acute deterioration values falling below a minimum change may trigger an alarm or be interpreted by a healthcare provider as an indication of the patient's declining physiologic stability, in some embodiments the change in slope or derivative of the slope of the predicted probability of acute deteriorations falling below a certain minimum may trigger an alarm or be interpreted by a healthcare provider as an indication of the patient's rapidly declining health. For example, if a patient is slightly declining and suddenly starts to decline at a much faster rate, this change in the acceleration of the slope may trigger an alarm. In some embodiments, the curvature of the predicted probability of acute deterioration plot may be provided, such as by a presentation and/or comparison module.

Many times a patient's health may be compromised in favor of conforming the patient's care to established pro form a health care best-practices and hospital logistics. For example, many hospitals require their healthcare workers to take a patient's vital signs every 2-4 hours, which requires awakening patients during the nighttime, which interferes with providing full sleep and enter deep sleep, which may be critical to a patient's recovery, and to draw blood from patients every day or two, which can be detrimental to an anemic or hemophiliac. If a patient's course has been so far unremarkable and yet the patient has an increasing predicted probability of acute deterioration, a healthcare worker may rely on the predicted probability of acute deterioration to determine whether or not a contemplated diagnostic test or optional therapeutic procedure may be deferred or omitted in order to allow the patient to better recover.

The system may include the ability to view a patient's prior hospital visits. In some embodiments, if a patient has a recurring condition, it may be preferable to view that patient's past PPOD values in addition to the present PPOD values, in order to anticipate what trajectories are likely to materialize for this patient in the current acute-care episode. Differences in data source (e.g., HL7 continuity-of-care CCD from a different institution where the patient previously received inpatient care) may be represented with unique point-icons or any other means of differentiating them, as not all embodiments are intended to be limited in these respects. In addition or alternatively, a physician or other provider may click on or hover over a graphed PPOD point to access additional information, such as the data inputted to calculate the PPOD value, or other information.

In some embodiments, the PPOD value or a timeseries comprised of serial PPOD values may be a medical reference "figure-of-merit" that is used by a health caregiver, such as a physician, nurse or other provider, to track the patient's risk of acute deterioration before, during or after a medical procedure or illness, in order to assist in preventing that patient from reaching a health crisis. When used in this manner, the PPOD display enables the attending physicians and nurses to detect trends in the patient's physiologic stability and hemodynamic compensatory ability over time, particularly in evaluating post-operative recovery in the hospital. It also provides a statistically significant "outcome" for both clinical studies and retrospective studies of the relative efficacies among various surgical procedures or techniques, and among medical treatments and drugs.

Figure 2A:
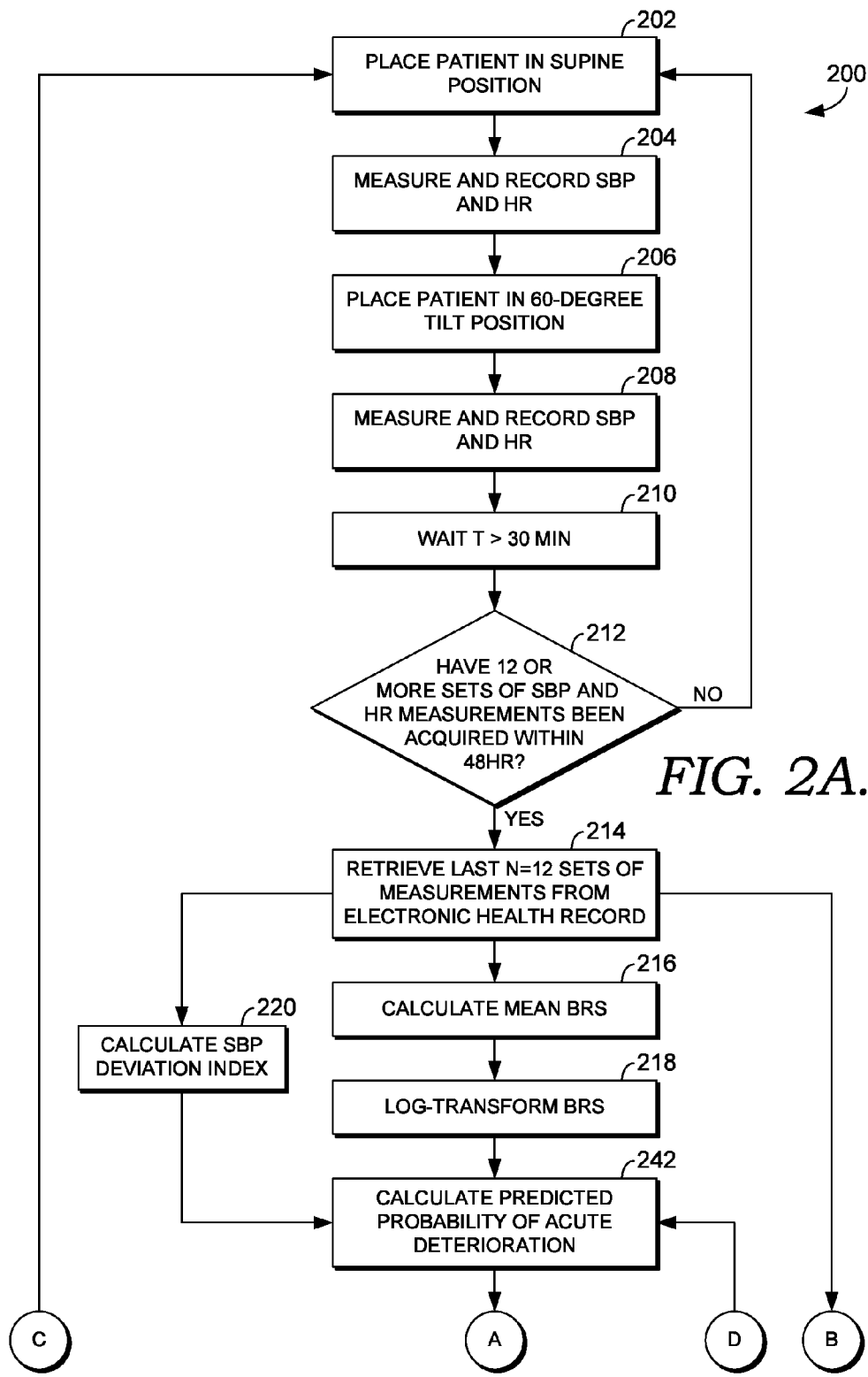
FIGS. 2A and 2B represent a flow diagram illustrating an exemplary process for determining a numerical probability of acute deterioration in hospitalized patients.
Figure 2B:
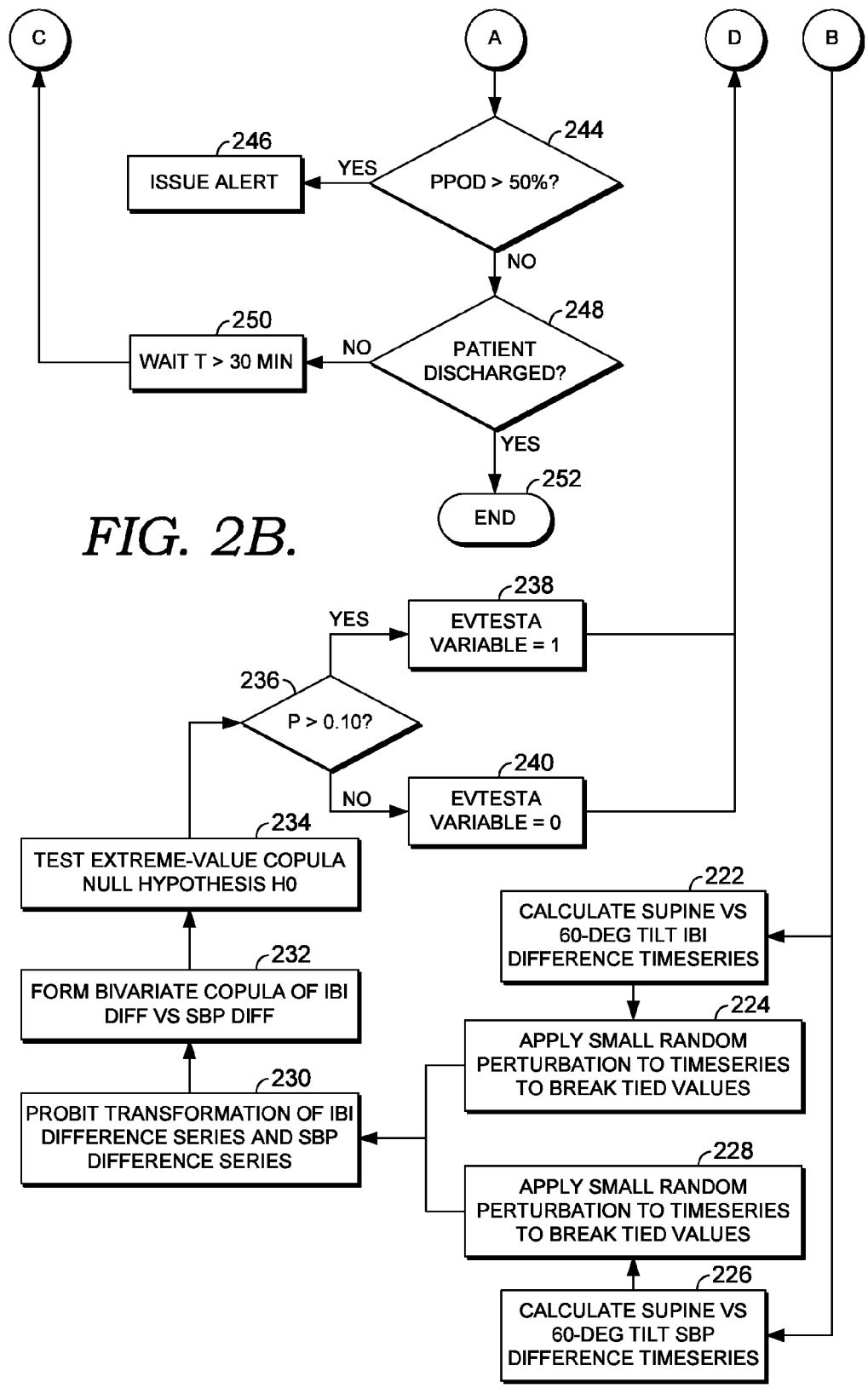

Turning now to FIGS. 2A and 2B, a flow diagram illustrates an exemplary process for determining a numerical probability of acute deterioration in hospitalized patients.

At step 202, a patient is placed in a supine position. In the supine position, at step 204, the SBP and heart rate for the patient is measured and recorded in an electronic health record or other patient record. At step 206, the patient is placed in a 60 degree (from supine) tilt position, and at step 208, the SBP and heart rate for the patient is measured and recorded (e.g., in the electronic health record). A time period of greater than 30 minutes is then observed, at step 210. Step 212 represents a decision point on whether the process of steps 202-210 has been maneuvered at least 12 times for the patient within a 48 hour time span. If the process has not been maneuvered at least 12 times within a 48 hour time span, then the process returns to step 202 to continue to build sets of SBP and heart rate for the patient in order to meet the requirement of 12 sets of measurements within a 48 hour time span. Otherwise, if the required steps of SBP and heart rate have been measured, the process moves from step 212 to step 214 where the last N=12 sets of measurements are retrieved from the patient's electronic health record.

The process then moves along three paths from step 214. Along one path, at step 216, a mean BRS is calculated for the patient. Then, at step 218, the calculated BRS is log-transformed.

Along another path, at step 220, the SBP deviation index is calculated.

Along yet another path, at step 222, a supine versus 60 degree tilt IBI difference timeseries is calculated. Then, at step 224, a small random perturbation to timeseries is applied to break tied values. Additionally, returning to step 214, a supine versus 60 degree tilt SBP difference timeseries, at step 226. Then, at step 228, a small random perturbation to timeseries is applied to break tied values.

The results of steps 224 and 228 are then combined, and then at step 230, a probit transformation is performed of IBI difference series and SBP difference series. At step 232, a bivariate copula of IBI difference versus SBP difference is formed. Step 234 involves testing extreme-value copula null hypothesis HO.

At determination is then made, at step 236, if P>0.10. If true, then at step 238, evTestA variable equals 1 and the process moves to step 242. Otherwise, if P>0.10 is false, then at step 240, evTestA variable equals zero and the process moves to step 242.

At step 242, the results from steps 218, 220, 238 and 240 are utilized to calculate the predicted probability of acute deterioration (PPOD) score. At step 244, it is determine whether the PPOD score is greater than, for instance, 50 percent. If so, then at step 246, an alert is issued (e.g., through an electronic health record system) to appropriate clinicians who are treating the patient, and can be displayed on various computing devices. Otherwise, if the PPOD score is below the set threshold for an alert (e.g., below 50 percent), then at step 248, it is determine whether the patient has been discharged. If the patient has been discharged, then the process ends at step 252. Otherwise, if the patient has not been discharged, then at step 250, time period of greater than 30 minutes is then observed and the process can return to step 202 for another set of measurements for eventually calculating another PPOD score through process 200.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

The invention claimed is:

1. Computer storage media, not being a transitory signal per se, storing computer-useable instructions that, when executed by one or more computing devices, cause the one or more computing devices to perform a method for determining a probability of acute deterioration for a particular patient, the method comprising:
receiving patient information comprising a plurality physiological measurements for a patient in anatomically challenged and unchallenged positions;
conditioning the patient information to create conditioned patient information; and
based on the conditioned patient information, determining a statistical probability of acute deterioration for the patient, wherein determining the statistical probability of acute deterioration involves determining a copula based on the conditioned patient information and determining that the copula is an extreme-value copula, wherein determining that the copula is an extreme-value copula involves comparing the determined copula to a rank-based nonparametric estimator of the patient's copula.

2. The media of claim 1, wherein the physiological measurements comprise systolic blood pressure (SBP) measurements and heart-rate measurements for the patient.

3. The media of claim 2, wherein the physiological measurements for the patient in anatomically challenged and unchallenged positions are derived from the patient in a supine position and a tilted position, respectively.

4. The media of claim 1 further comprising selectively providing a notification based on the determined statistical probability of acute deterioration.

5. The media of claim 1, wherein the plurality of physiological measurements comprises a timeseries of measurements with timeseries intervals greater than 30 minutes.

6. The media of claim 1, wherein conditioning the patient information includes determining an index of deviation of the patient's current SBP from the patient's usual SBP.

7. The media of claim 6, wherein conditioning the patient information further includes determining a baroreceptor reflex sensitivity (BRS).

8. The media of claim 1, wherein conditioning the patient information includes determining an anatomically challenged vs. unchallenged heart-beat interval difference timeseries and determining an anatomically challenged vs. unchallenged SBP difference timeseries.

9. The media of claim 1, wherein the statistical probability of acute deterioration for the patient comprises a score.

10. The media of claim 1, wherein the predicted probability of acute deterioration is determined from by logistic regression, K-nearest neighbor clustering, neural-network, support-vector machine classifier, or other statistical techniques.

11. The media of claim 1, further comprising determining a predicted length of stay for the patient, based at least in part on the determined probability of acute deterioration for the patient.

12. The media of claim 1, further comprising allocating healthcare resources for treating the patient, based at least in part on the determined probability of acute deterioration for the patient.

13. The media of claim 4, wherein the notification comprises a visual or audible alert, email, SMS text message, or electronic notification provided to a caregiver for the patient.

14. A method to prevent acute deterioration of health in a population of patients, the method comprising:
providing an electronic notification to caregivers of a set of members of the population who exhibit above-threshold values of a predicted probability of acute deterioration (PPOD) score calculated from a timeseries of physiological measurements acquired from a patient in anatomically challenged and unchallenged positions,
wherein a calculation of the PPOD score involves determining a probability that a copula of an anatomically challenged vs. unchallenged heart rate difference timeseries and an anatomically challenged vs. unchallenged systolic blood pressure difference timeseries is an extreme-value copula, and
wherein determining that the copula is an extreme-value copula involves comparing the determined copula to a rank-based nonparametric estimator of the patient's copula.

15. The method of claim 14, wherein calculating the PPOD score involves computation of a baroreceptor reflex sensitivity and an index of the deviation of the patient's current systolic blood pressure from the pressure that is usual for the patient.

16. A computer-implemented method for providing a predicted probability of acute deterioration for a particular patient comprising:
receiving patient-specific data from a health record, the data comprising plurality of physiological measurements;
conditioning the patient-specific data to create conditioned data;
calculating, from the conditioned data, a predicted probability of acute deterioration for the particular patient by applying logistic regression, K-nearest neighbor clustering, neural network, support-vector machine classifier, or other statistical technique, wherein the calculation of the predicted probability of acute deterioration for the particular patient involves determining a copula based on the conditioned data and determining that the copula is an extreme-value copula, wherein determining that the copula is an extreme-value copula involves comparing the determined copula to a rank-based nonparametric estimator of the patient's copula; and
selectively providing a notification based on the calculated predicted probability of acute deterioration.

17. The computer-implemented method of claim 16, wherein the calculation of a predicted probability of acute deterioration for the particular patient further involves computation of a baroreceptor reflex sensitivity and an index of the deviation of the patient's current systolic blood pressure from the pressure that is usual for the patient.

* * * * *